(12) United States Patent
Samarao et al.

(10) Patent No.: US 10,036,717 B2
(45) Date of Patent: Jul. 31, 2018

(54) NANOSTRUCTURED LANTHANUM OXIDE HUMIDITY SENSOR

(71) Applicant: Robert Bosch GmbH, Stuttgart (DE)

(72) Inventors: Ashwin K. Samarao, Sunnyvale, CA (US); Gary O'Brien, Palo Alto, CA (US); Ando Feyh, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/540,235

(22) PCT Filed: Dec. 28, 2015

(86) PCT No.: PCT/US2015/067685
§ 371 (c)(1),
(2) Date: Jun. 27, 2017

(87) PCT Pub. No.: WO2016/109434
PCT Pub. Date: Jul. 7, 2016

(65) Prior Publication Data
US 2017/0370864 A1    Dec. 28, 2017

Related U.S. Application Data

(60) Provisional application No. 62/097,496, filed on Dec. 29, 2014.

(51) Int. Cl.
*H01C 7/00*      (2006.01)
*G01N 27/12*    (2006.01)
(Continued)

(52) U.S. Cl.
CPC .......... *G01N 27/121* (2013.01); *G01N 27/07* (2013.01); *G01N 27/14* (2013.01); *C01F 17/0043* (2013.01)

(58) Field of Classification Search
CPC ....... G01N 27/121; G01N 27/07; G01N 27/14
(Continued)

(56) References Cited

U.S. PATENT DOCUMENTS 4,263,576 A * 4/1981 Murata ................ G01N 27/121
                                                                252/519.12
4,928,513 A * 5/1990 Sugihara ................ G01N 27/12
                                                                338/34
(Continued)

FOREIGN PATENT DOCUMENTS

WO        2013/191309 A1    12/2013

OTHER PUBLICATIONS

International Search Report corresponding to PCT Application No. PCT/US2015/067685, dated Apr. 14, 2016 (3 pages).

*Primary Examiner* — Kyung Lee
(74) *Attorney, Agent, or Firm* — Maginot Moore & Beck LLP

(57) ABSTRACT

A thin film gas sensor device includes a substrate, a nanostructured thin film layer, and a first and a second electrode. The nanostructured thin film layer is supported by the substrate and is formed with a semi-conductor material including holes. The semiconductor material is configured to undergo an increase in a density of the holes in the presence of a target gas, thereby decreasing an electrical resistance of the nanostructured thin film layer. The first and the second electrodes are supported by the substrate and are operably connected to the nanostructured thin film layer, such that the decrease in electrical resistance can be detected.

13 Claims, 8 Drawing Sheets

(51) Int. Cl.
*G01N 27/07* (2006.01)
*G01N 27/14* (2006.01)
*C01F 17/00* (2006.01)

(58) Field of Classification Search
USPC .......................................................... 338/35
See application file for complete search history.

(56) References Cited

U.S. PATENT DOCUMENTS

| | | | |
|---|---|---|---|
| 6,134,946 A | 10/2000 | Liu et al. | |
| 8,003,513 B2 * | 8/2011 | Shah | H01L 21/4857 |
| | | | 257/758 |
| 2010/0307238 A1 * | 12/2010 | Van Popta | G01N 27/225 |
| | | | 73/335.04 |
| 2012/0272721 A1 | 11/2012 | Kochupurackal et al. | |
| 2014/0167791 A1 * | 6/2014 | Feyh | G01N 27/121 |
| | | | 324/694 |
| 2014/0223997 A1 | 8/2014 | Gole | |
| 2015/0118111 A1 * | 4/2015 | Samarao | G01N 27/227 |
| | | | 422/90 |
| 2015/0137836 A1 * | 5/2015 | Kim | G01N 27/127 |
| | | | 324/693 |

* cited by examiner

NANOSTRUCTURED LANTHANUM OXIDE HUMIDITY SENSOR

This application is a 35 U.S.C. § 371 National Stage Application of PCT/US2015/067685, filed on Dec. 28, 2015, which claims the benefit of priority of U.S. provisional application serial no. 62/097,496, filed on Dec. 29, 2014, the disclosures of which are herein incorporated by reference in their entirety.

FIELD

This disclosure relates generally to sensor devices and particularly to thin-film gas sensor devices.

BACKGROUND

Semiconductor gas sensors are used to detect the presence of a particular gas or gasses in an environment to which the sensor is exposed. A common type of gas sensor is a metal oxide semiconductor (MOS) gas sensor. MOS gas sensors, which are also referred to as "thick film" MOS gas sensors, typically include a gas-sensitive portion located between two electrodes. The gas-sensitive portion is a polycrystalline thick-film that is configured to undergo a change in optical transmittance, electrode, and/or ionic conduction in the presence of the target gas. The change of the gas-sensitive portion is detected by an external circuit that is operably connected to the gas sensor.

One type of thick film MOS gas sensor device is a hygrometer, which is also referred to as a humidity sensor. Humidity sensors are configured to sense the moisture content (including water vapor) of an atmosphere and are used in applications including automotive, greenhouses, saunas, and museums. In most applications, it is desirable for a humidity sensor to be small, inexpensive, accurate, and electrically efficient. It is also desirable for the humidity sensor to quickly determine the concentration of moisture in a selected environment. That is, the humidity sensor should have a fast response time.

Some known types of MOS humidity sensors are capacitive based and include a gas sensitive portion formed from an organic polymer configured to exhibit an electrical/ionic change in response to a change in humidity. An external read out circuit senses the electrical/ionic response as a change in capacitance. These types of humidity sensors typically have a slower than desired response time, and the external read out circuit for sensing the change in capacitance is somewhat complex and expensive. Therefore, for at least some of the above-described reasons, further developments in the area of humidity sensors are desirable.

SUMMARY

According to an exemplary embodiment of the disclosure, a thin film gas sensor device includes a substrate, a nanostructured thin film layer, and a first and a second electrode. The nanostructured thin film layer is supported by the substrate and is formed with a semi-conductor material including holes. The semiconductor material is configured to undergo an increase in a density of the holes in the presence of a target gas, thereby decreasing an electrical resistance of the nanostructured thin film layer. The first and the second electrodes are supported by the substrate and are operably connected to the nanostructured thin film layer, such that the decrease in electrical resistance can be detected.

In one embodiment, the nanostructured thin film layer is configured to undergo the decrease in the electrical resistance during a time constant, and the time constant is less than one second.

In another embodiment, the nanostructured thin film layer is non-organic and does not include polyimide or other polymers.

In yet another embodiment, the nanostructured thin film layer is formed from lanthanum oxide and the target gas is water vapor.

In one embodiment, the thin film gas sensor device further includes a non-suitable seed layer supported by the substrate. The nanostructured thin film layer is formed with atomic layer deposition directly on the non-suitable seed layer. Also, the nanostructured thin film layer defines a plurality of grain boundaries formed by spaced-apart nucleation on the non-suitable seed layer, and air spaces are defined between at least some grains of the plurality of grains.

According to another exemplary embodiment of the disclosure, a method of fabricating a thin film gas sensor device comprises providing a substrate, supporting a first electrode with the substrate, supporting a second electrode with the substrate, and forming a nanostructured thin film layer using a semi-conductor material including holes. The semiconductor material is configured to undergo an increase in a density of the holes in the presence of a target gas, thereby decreasing an electrical resistance of the nanostructured thin film layer. The method further includes operably connecting the first and the second electrodes to the nanostructured thin film layer, such that the decrease in electrical resistance can be detected.

In one embodiment, the method further includes forming the nanostructured thin film layer from lanthanum oxide, such that the decrease in electrical resistance occurs in response to the target gas including water vapor.

In another embodiment, the method further includes forming the nanostructured thin film layer so as to cause the nanostructured thin film layer to undergo the decrease in electrical resistance during a time constant of less than one second.

In yet another embodiment, the method further includes forming the nanostructured thin film layer with non-organic material and without polyimide or other polymers.

In one embodiment, the method further includes forming a non-suitable seed layer above the substrate, and forming the nanostructured thin film layer using ALD directly on the non-suitable seed layer. The method also includes forming a heater layer above the substrate, and forming the non-suitable seed layer above the heater layer. The method further includes forming the first electrode and the second electrode directly on the non-suitable seed layer.

In a further embodiment, forming the nanostructured thin film layer further comprises forming a plurality of grains of the nanostructured thin film layer by spaced-apart nucleation of the semiconductor material of the nanostructured thin film layer on the non-suitable seed layer. The method further includes structuring the non-suitable seed layer to encourage the spaced-apart nucleation of the plurality of grains of the sensing layer. The structuring of the non-suitable seed layer comprises ion-milling or chemically activating the non-suitable seed layer.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
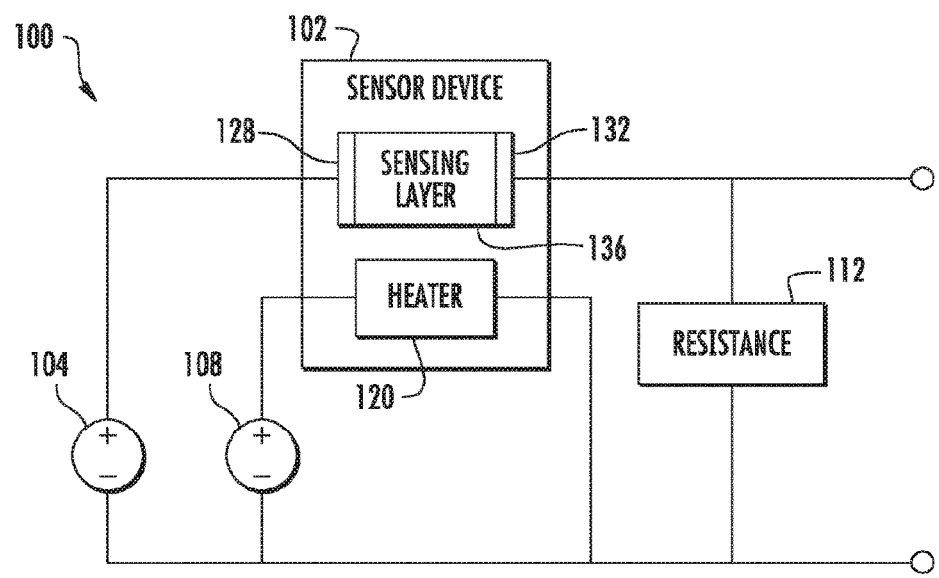
FIG. 1 is a block diagram of an exemplary semiconductor sensor device, according to the disclosure, shown as a thin film gas sensor device.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

As shown in FIG. 1, an exemplary embodiment of a sensor system 100, as described herein, includes a thin film gas sensor device 102 shown electrically connected to a sensor voltage source 104, a heater voltage source 108, and a resistance 112. The voltage sources 104, 108 are DC voltage sources, which are configured to maintain a desired magnitude of voltage. The resistance 112 provides a magnitude of known electrical resistance and is formed from any electrically resistive device, as desired by those of ordinary skill in the art.

Figure 2:
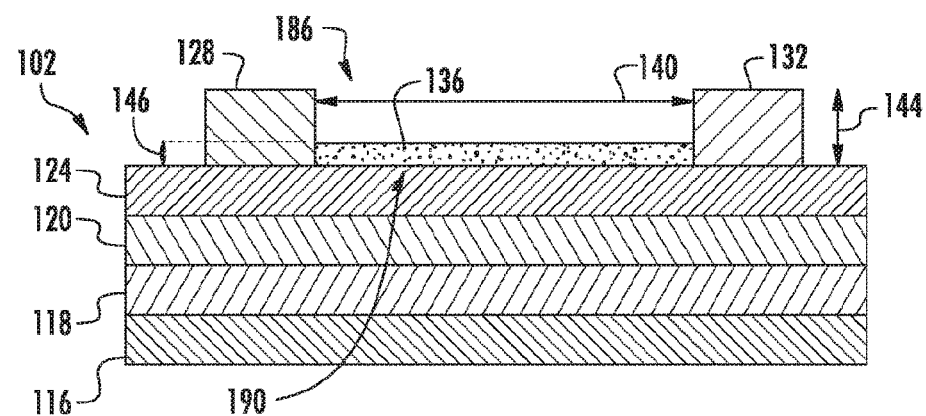
FIG. 2 is a cross sectional view of the thin film gas sensor device of FIG. 1, showing a gas-sensing layer of lanthanum oxide that has been formed using atomic layer deposition (ALD)

With additional reference to FIG. 2, the thin film gas sensor device 102 includes a handle layer 116, a buried oxide layer 118, a heater layer 120, a seed layer 124, two electrodes 128, 132, and a sensing layer 136. The handle layer 116 is typically formed from a layer of silicon as is provided in a typical silicon on insulator (SOI) wafer. The handle layer 116 is also referred to herein as a substrate.

The oxide layer 118 is located between the handle layer 116 and the heater layer 120 and is configured to isolate the handle layer from the heater layer. The oxide layer 118 is formed from silicon dioxide ($SiO_2$), sapphire, or another suitable insulative material.

The heater layer 120 is formed on the oxide layer 118 and is electrically connected to the voltage source 108. The heater layer 120, also referred to herein as a joule heater, is formed from a material that generates heat when exposed to an electrical current or other form of energy. The heater layer 120 is configured to heat the sensing layer 136 to a desired temperature. In the illustrated embodiment, the handle layer 116, the oxide layer 118, and the heater layer 120 are formed from a typical SOI wafer with the heater layer 120 being the "device layer" of the SOI wafer. Accordingly, the heater layer 120, in at least one embodiment, is formed from silicon. Other suitable materials for forming the heater layer 120 include doped silicon, composite materials, ALD deposited platinum, and other suitably electrically conductive materials.

As shown in FIG. 2, the seed layer 124 is formed on the heater 120 and is located above the substrate 116. The seed layer 124, in one embodiment, is selected to interact with the sensing layer 136 in a "suitable" manner that results in a generally contiguous layer of the material of the sensing layer. In another embodiment, the seed layer 124 is formed from a material that is selected to interact with the sensing layer in an "unsuitable" or "non-suitable" manner that encourages nucleation of the sensing layer 136 at spaced-apart, isolated, and/or sporadic nucleation sites 182 (FIG. 3) (collectively referred to herein as "spaced apart") on the seed layer. In such embodiment, the seed layer 124 may be thermal silicon dioxide.

Additionally, the seed layer 124 may be structured with trenching (or any other desired process) to further encourage spaced-apart nucleation of the sensing layer 136. In one specific embodiment, the "structuring" includes patterning the seed layer 124 and/or chemically activating certain spaced-apart nucleation sites 182 in order to encourage spaced-apart nucleation of the sensing layer 136. In yet another embodiment, the "structuring" includes ion-milling the seed layer 124 with passive gasses, such as argon, to make the seed layer more dense or less dense at spaced-apart nucleation sites 182, thereby resulting in selective encouragement of spaced-apart nucleation of the sensing layer 136. In general, the seed layer 124 is formed and/or structured from any material(s) and by any process(s) that encourages a desired level of spaced-apart nucleation of the sensing layer 136 on the seed layer.

The electrodes 128, 132 are formed above the seed layer 124 from an electrically conductive material using any process as desired by those of ordinary skill in the art. In one embodiment, the electrodes 128, 132 are formed from platinum and are electrically isolated from each other. The electrodes 128, 132 are spaced-apart from each other by a distance 140, and define a height 144. The distance 140 and the height 144 are selected based on the gas to be sensed/detected (referred to herein as a target gas), the material of the sensing layer 136, the structure of the sensing layer, and the application of the sensor device 102, among other considerations. Although the sensor device 102 is shown as including two of the electrodes 128, 132, in other embodiments, the sensor device includes any number of electrodes, as desired by those of ordinary skill in the art.

With continued reference to FIG. 2, the sensing layer 136, which is also referred to herein as a nanostructured thin film layer, is supported by the substrate and formed directly on the seed layer 124 between the electrodes 128, 132. In one embodiment, the sensing layer 136 is formed with a semiconductor material including holes, and the semiconductor material is configured to undergo an increase in a density of the holes in the presence of a target gas (such as water vapor), thereby decrease an electrical resistance of the sensing layer 136. The sensing layer 136 is operably connected to the electrodes 128, 132 so that electrical current is able to flow between the electrodes through the sensing layer and so that the decrease in electrical resistance of the sensing layer 136 can be detected. The sensing layer 136 defines a width 140 and a thickness 146. The thickness 146 of the sensing layer 136 is less than the thickness 144 of the electrodes 128, 132. In one embodiment, the thickness 146 of the sensing layer 136 is between approximately ten nanometers to approximately one hundred nanometers. Depending on the desired application of the sensor device 102, the thickness 146 may be outside of the exemplary range. The sensing layer 136 is formed from ALD deposited lanthanum oxide. The sensing layer 136 and the electrodes 128, 132 are serially connected to the resistance 112 and to the voltage source 104.

Figure 3:
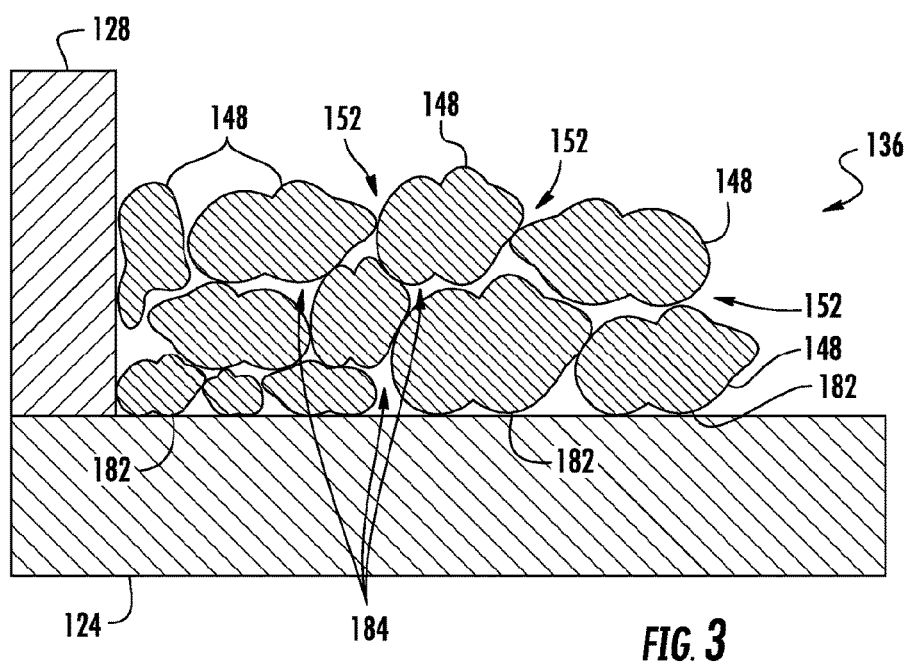
FIG. 3 is a depiction of a portion of the thin film gas sensor device of FIG. 1, showing grains and grain boundaries of a portion of the gas-sensing layer.

As shown in FIG. 3, in one embodiment, the sensing layer 136 is a porous structure that is formed from a plurality of grains 148, which are also referred to herein as crystallites. In general, each grain 148 contacts at least one other grain at a junction referred to as a grain boundary 152 (some of which are identified in FIG. 3). Air spaces 184 formed between the grains 148 at least partially determine the porosity of the sensing layer 136. The grains 148 are configured, in one embodiment, to form as many grain boundaries 152 as possible, so that the sensing layer 136 provides more surface area per gram of material, as compared to prior art sensing layers, thereby resulting in better sensitivity of the sensor device 102. Accordingly, the grains 148 of the sensing layer 136 enable the sensing layer to, in general, be thinner and smaller than prior art sensing layers/sensing portions, but have at least as many or more grain boundaries 152. In another embodiment, the sensing layer 136 is a substantially non-porous structure in which the grains 148 are packed tightly together and substantially no air spaces 184 are present.

Figure 4:
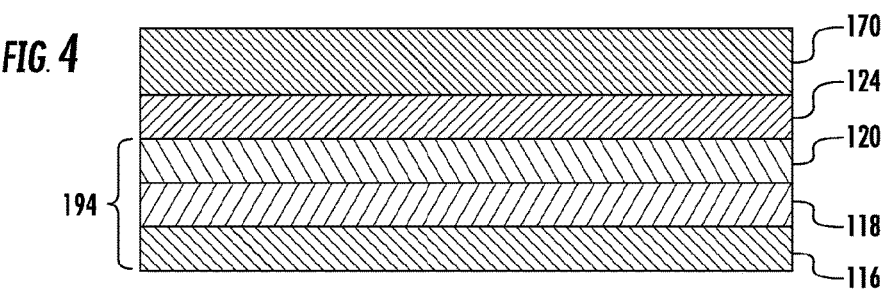
FIG. 4 is a cross sectional view of a portion of the thin film gas sensor device of FIG. 1, showing a substrate layer, an oxide layer, a heater layer, a seed layer, and a sacrificial material.

With reference to FIG. 4 fabricating the sensor device 102, in an exemplary embodiment, begins by providing an SOI wafer 194 that includes the handle layer 116, the oxide layer 118, and a device layer that is configured as the heater 120.

Next, the seed layer 124 is applied to the heater 120 using any process as desired by those of ordinary skill in the art. In one embodiment, the material of the seed layer 124 is selected to react with the material of the sensing layer (i.e. lanthanum oxide) to achieve a desired porosity of the sensing layer 136 and/or a desired size of the grains 148 of the sensing layer 136. In such an embodiment, the material of the seed layer 124 is selected to be a "non-suitable" material. The term "non-suitable material" is defined herein as a material that when used as a seed layer for a particular sensor layer material, causes spaced-apart nucleation of the grains 148 during depositing/formation of the sensing layer 136. In another embodiment, the material of the seed layer 124 is selected as a "suitable material" that results in a substantially contiguous layer of the sensing material during depositing/formation of the sensing layer 136.

Next, a sacrificial material 170 is applied to the seed layer 124. The sacrificial material 170 is deposited/formed on the seed layer 124 using any process, as desired by those of ordinary skill in the art.

Figure 5:
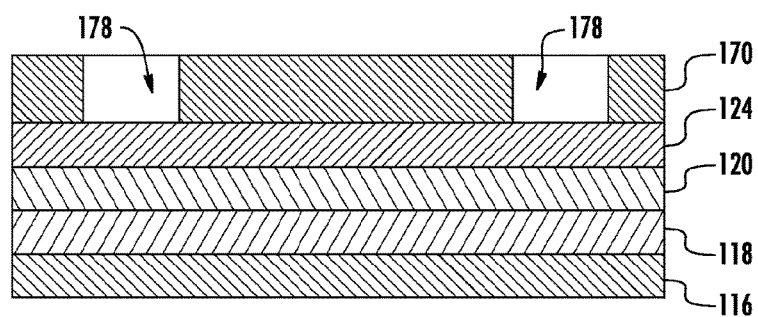
FIG. 5 is a cross sectional view of a portion of the thin film gas sensor device of FIG. 1, showing trenches etched in the sacrificial material.

With reference to FIG. 5, a mask (not shown) is applied to the sacrificial material 170 in a pattern that is configured to define openings (not shown) that correspond to the electrodes 128, 132. Thereafter, the sacrificial material is patterned/trenched through a wet or dry etching process or any other process as desired by those of ordinary skill in the art. After the patterning, the mask is removed and the sacrificial material 170 defines a well 178 for each electrode 128, 132.

Figure 6:
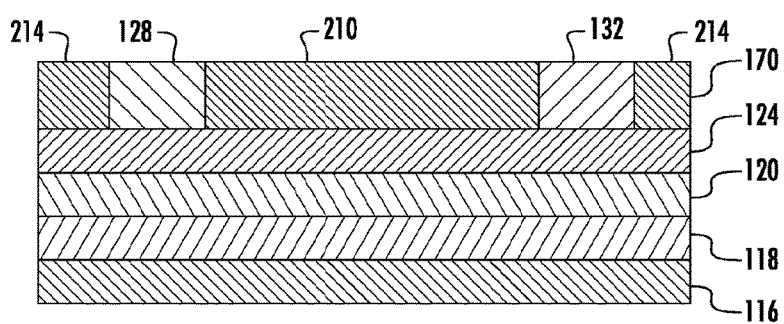
FIG. 6 is a cross sectional view of a portion of the thin film gas sensor device of FIG. 1, showing electrodes formed in the trenches of the sacrificial material.

Next, as shown FIG. 6, the material of the electrodes 128, 132 is applied to the wells 178, using any process as desired by those of ordinary skill in the art. The material of the electrodes 128, 132 at least partially fills the wells 178 and takes the shape of the wells. In some processes, chemical-mechanical planarization (CMP) may be conducted resulting in a desired height of the electrodes 128, 132.

Figure 7:
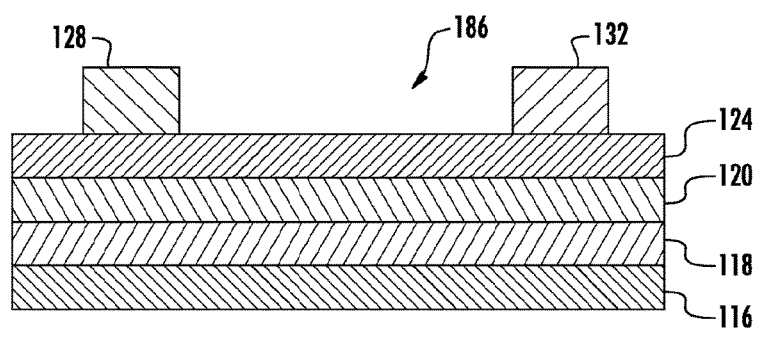
FIG. 7 is a cross sectional view of a portion of the thin film gas sensor device of FIG. 1, after removal of the sacrificial material.

Next, with reference to FIG. 7, the sacrificial material 170 is removed from the seed layer 124 leaving the electrodes 128, 132 formed on the seed layer. Additionally, the removal of the sacrificial layer 170 forms a well 186 between the electrodes 128, 132 for receiving the material of the sensing layer 136. In one embodiment, only the portion of the sacrificial material 170 located between the electrodes 128, 132 is removed.

With reference again to FIG. 2, next the sensing layer 136 is formed on the seed layer 124 in the well 186 defined between the electrodes 128, 132. ALD is used to form the sensing layer 136 from lanthanum oxide. The lanthanum oxide reacts with the material of the seed layer 124 to achieve the desired porosity of the sensing layer 136. Accordingly, in one embodiment, the ALD deposited lanthanum oxide reacts with a non-suitable material of the seed layer 124 resulting in the formation of grains 148 of lanthanum oxide having a desired size and resulting in a desired porosity of the sensing layer 136. In another embodiment, the ALD deposited lanthanum oxide reacts with a suitable material of the seed layer 124 resulting in the formation of tightly packed grains 148 of lanthanum oxide that form a substantially continuous layer of nanostructured lanthanum oxide.

ALD is used to deposit materials by exposing a substrate to several different precursors sequentially. A typical deposition cycle begins by exposing a substrate to a precursor "A" which reacts with the substrate surface until saturation. This is referred to as a "self-terminating reaction." Next, the substrate is exposed to a precursor "B" which reacts with the surface until saturation. The second self-terminating reaction reactivates the surface. Reactivation allows the precursor "A" to react with the surface. Typically, the precursors used in ALD include an organometallic precursor and an oxidizing agent such as water vapor or ozone. In one embodiment, precursors such as tris-(i-propylcyclopentadienyl)-lanthanum and oxygen plasma are used to form the ALD deposited lanthanum oxide sensing layer 136.

The deposition cycle results, ideally, in one atomic layer of lanthanum oxide being formed on the substrate. Thereafter, another layer may be formed by repeating the process. Accordingly, the final thickness of the layer is controlled by the number of cycles the substrate is exposed to. Moreover, deposition using an ALD process is substantially unaffected by the orientation of the particular surface upon which material is to be deposited. Accordingly, an extremely uniform thickness of material may be realized both on the upper and lower horizontal surfaces and on the vertical surfaces.

As described above, the material of seed layer 124 affects the resultant porosity of the sensing layer 136. Typically, ALD is used to deposit a generally contiguous (non-porous) thin film of a material onto a seed layer formed from a suitable material. It has been determined, however, that the structure of the material deposited using ALD, is heavily dependent on the interaction of the deposited material with the material forming the seed layer. In particular, if the seed layer 124 is formed from a non-suitable material, the seed layer causes nucleation of the grains 148 of the deposited sensing material at the spaced-apart nucleation sites 182 (FIG. 3). Accordingly, the grains 148 grow in far-isolated "islands" with numerous air spaces 184 (FIG. 3) therebetween, thereby defining a porosity of the sensing layer 136. The grains 148 contact each other at many grain boundaries 152, which promotes adsorption (including chemisorption and heterogeneous catalysis) of the target gas. The selection of the seed material of the seed layer 124 and the number of cycles of ALD performed is based on at least the desired size of the grains 148, the density of the grains, the thickness of the sensing layer 136, the desired number of grain boundaries 152, and the desired porosity of the sensing layer 136.

Figure 8:
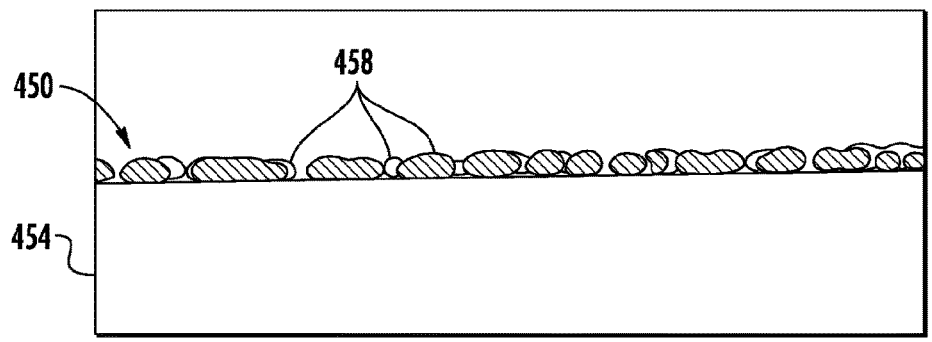
FIG. 8 is a depiction of a transmission electron microscope view of a platinum layer formed using a process that is suitable for forming the ALD deposited gas-sensing layer of FIG. 2, the platinum layer is shown as having a first average grain size and a first porosity.
Figure 9:
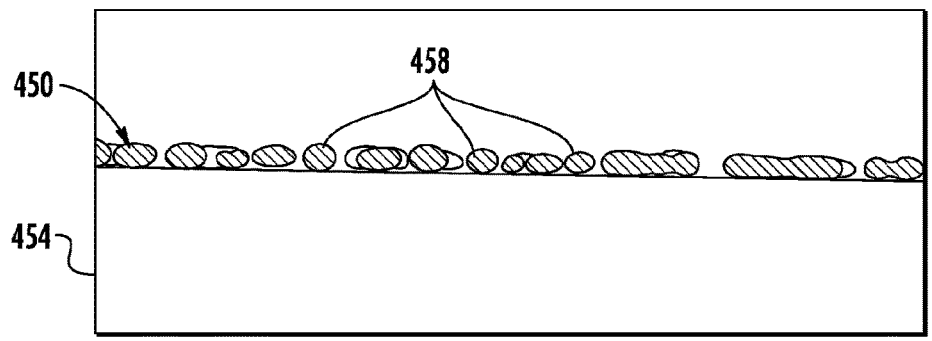
FIG. 9 is another depiction of a transmission electron microscope view of a platinum layer formed using the process that is suitable for forming the ALD deposited gas-sensing layer of FIG. 2, the platinum layer is shown as having a second average grain size that is less than the first average grain size and a second porosity that is greater than the first porosity.

FIGS. 8 and 9 show two microscope views of a sensing layer 450 that has been ALD deposited onto a non-suitable seed layer 454. In this example, the seed layer 454 is formed from silicon dioxide and the deposited material of the sensing layer 450 is platinum (Pt). In FIG. 8, approximately one hundred fifty cycles of ALD were performed at approximately 270° C. In FIG. 9, approximately one hundred twenty five cycles of ALD were performed at approximately 270° C. The reduction in cycles results in smaller grains 458 and more space between each grain (i.e. a higher porosity). Using ALD to deposit material in this manner, results in a sensing layer 136 that includes large amounts of three-interface regions between gas, metal/metal oxide, and the seed layer.

In operation, the sensor device 102 is configured to sense the presence of water vapor or humidity in an environment in which the sensor device is located or exposed. Due to the small size of the sensor device 102, as compared to prior art MOS gas sensors, it is usable to detect gasses in a variety of applications such as automobile exhaust systems, home appliances, laptops, handheld or portable computers, mobile telephones, smart phones, wireless devices, tablets, personal data assistants (PDAs), portable music players, film cameras, digital cameras, GPS receivers and other satellite navigation systems, electronic reading displays, projectors, cockpit controls, game consoles, earpieces, headsets, hearing aids, wearable display devices, security systems, and other applications as desired by those ordinary skill in the art. In one embodiment, the sensor device 102 measures approximately two millimeters by three millimeters by one millimeter, but may be either smaller or larger depending on the desired application.

Use of the sensor device 102 includes applying voltage from the voltage source 104 to the electrode 128, the sensing layer 136, the electrode 132, and the resistance 112. The voltage from the voltage source 104 establishes an electrical current (referred to as a sensor current) through the electrodes 128, 132, the sensing layer 136, and the resistance 112. The magnitude of the sensor current is based on at least the combined resistance of the electrodes 128, 132, the sensing layer 136, and the resistance 112, and is the same through the electrodes 128, 132, the sensing layer 136, and the resistance 112.

Next, the sensor device 102 is exposed to a space in which the target gas (water vapor) may or may not be present. The sensor device 102 and the resistance 112 form a voltage divider circuit, and an external circuit (not shown) monitors a voltage drop across the resistance 112 to determine if the target gas is present in the space. To reset the sensor device 102, a current is applied to the heater layer 120 in order to heat the sensing layer 136 and to evaporate any water that has accumulated thereon.

Figure 10:
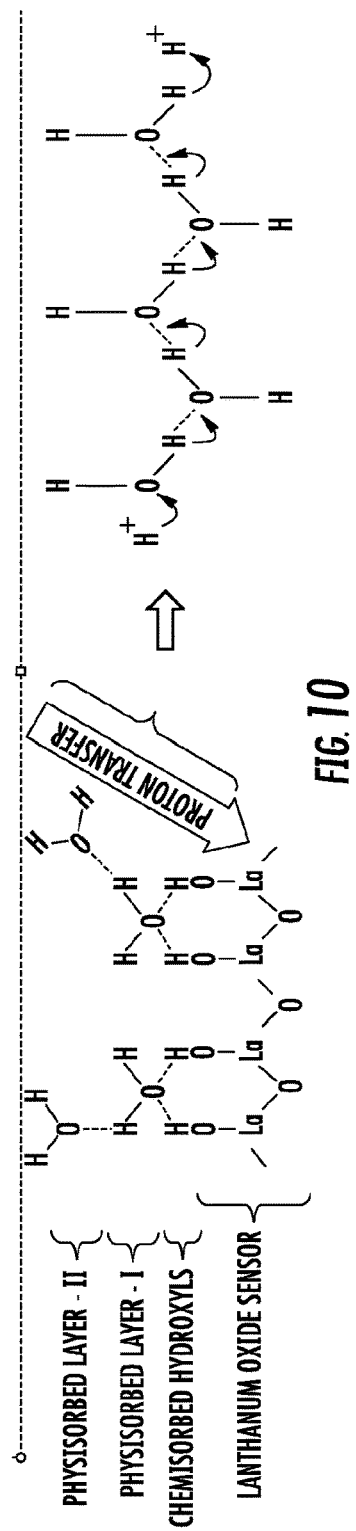
FIG. 10 is a diagram illustrating chemical reactions that occur in response to $OH^-$ hydroxyl groups of moisture combining with $La^{3+}$ cations on the surface of a lanthanum oxide gas-sensing layer.
Figure 11:
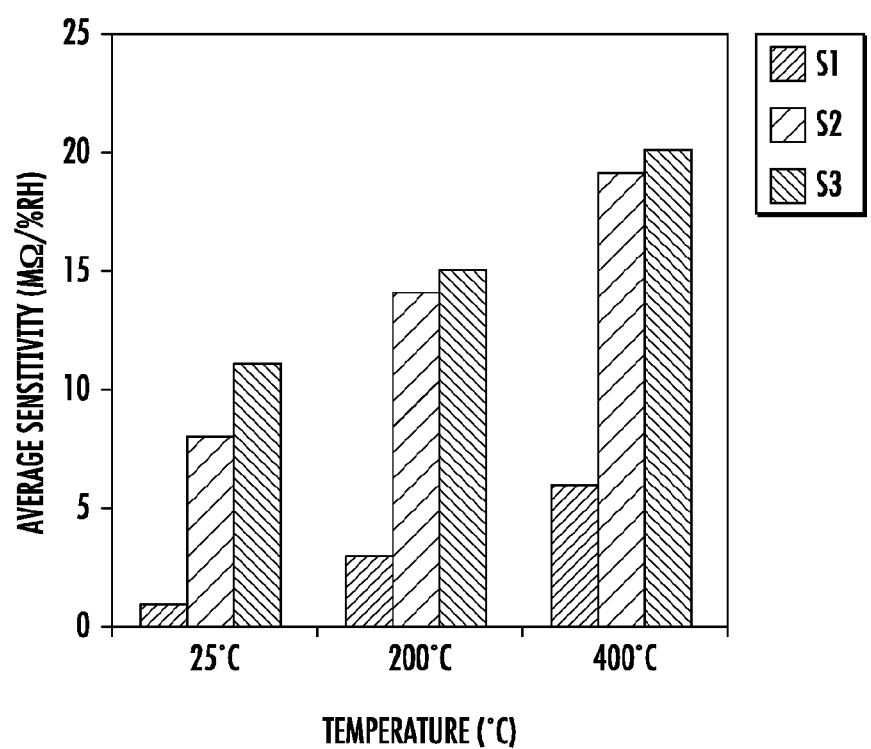
FIG. 11 is a graph of average sensitivity for sensing layers of three different materials including niobium pentoxide $Nb_2O_5$ (Code S1), neodymium oxide $Nd_2O_3$ (Code S2), and lanthanum oxide (Code S3) for three different annealing temperatures of 25° C., 200° C., 400° C.

With reference to FIG. 10, the sensor device 102 having an ALD deposited lanthanum oxide sensing layer 136 works according to the following principle. It is known that $OH^-$ hydroxyl groups of moisture readily combine with $La^{3+}$ cations on the surface of lanthanum oxide resulting in a subsequent dissociation of a water molecule. The dissociated water molecule provides a proton for electron conduction in the lanthanum oxide resulting in a reduced electrical resistance of the lanthanum oxide. The dissociated water molecules form a first layer of water molecules which are chemisorbed. Each subsequent layer of dissociated water molecules are physisorbed. The proton transfer process continues through subsequent layers of water molecules via the Grotthuss Chain Reaction. Thus, in response to increasing levels of humidity (water vapor) the electrical resistance of the lanthanum oxide sensing layer 136 is reduced. The reduction in electrical resistance is sensed by the external readout circuit by monitoring the voltage drop across the resistance 112. When the sensor device 102 is reset the dissociated water molecules are evaporated and the electrical resistance of the sensing layer 136 increases.

The sensor device 102 offers advantages over prior art humidity sensors. First, the sensing layer 136 formed from lanthanum oxide is non-organic, unlike polyimide and other polymer based humidity sensors. The sensor device 102 does not include polyimide or other polymers. Accordingly, the sensor device 102 is more robust than polymer based humidity sensors and has a much faster response time compared to polymer based humidity sensors. For example, in one embodiment the sensor device 102 has a time constant of less than one second, meaning that the sensing layer 136 undergoes the decrease in electrical resistance during the time constant. The time constant begins when the sensor device is exposed to the target gas and ends when a gas response percentage of the sensor device 102 is at approximately 90%. Additionally, the resistance based read out circuit suitable for use with the sensor system 100 is typically simpler and less expensive than the capacitive based read out circuits used with some thick film MOS humidity sensors.

Forming the sensing layer 136 using ALD is easier and more economical than known methods of forming a thick film of lanthanum oxide. For example, in the past groups have prepared lanthanum oxide for growing into a thick film by powering the lanthanum oxide with vigorous grinding and then converting the ground material into pellets by applying uniaxial pressure of 616 MPa to the ground material with a hydraulic pressing machine. This tedious process can be eliminated by forming the lanthanum oxide sensing layer 136 using ALD.

Figure 12:
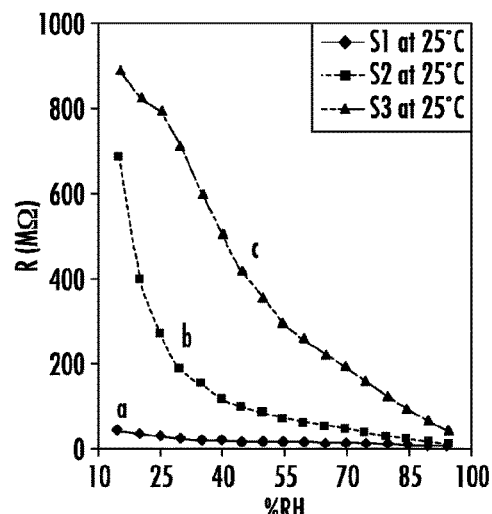
FIG. 12 is a graph of resistance versus percent relative humidity for the three different materials of FIG. 11 having been annealed at 25° C.
Figure 13:
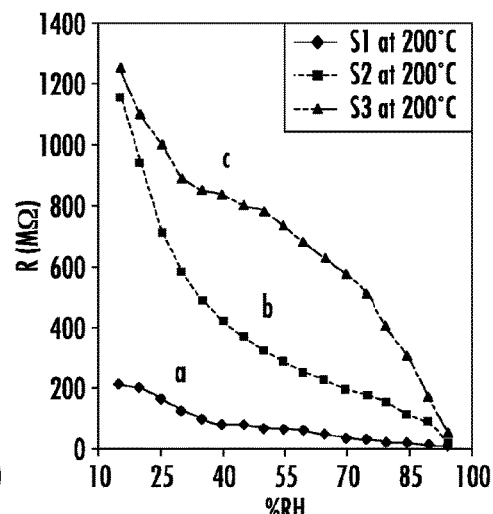
FIG. 13 is a graph of resistance versus percent relative humidity for the three different materials of FIG. 11 having been annealed at 200° C.
Figure 14:
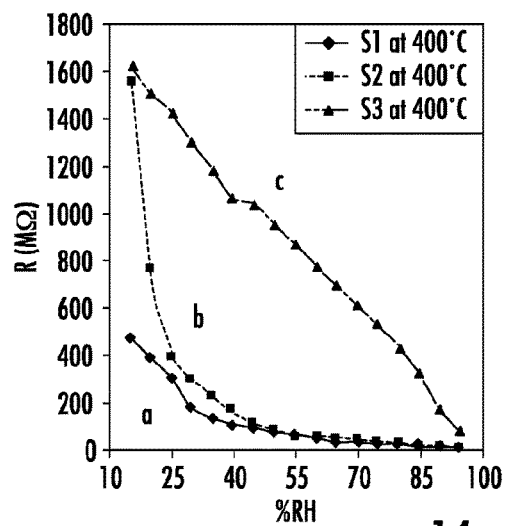
FIG. 14 is a graph of resistance versus percent relative humidity for the three different materials of FIG. 11 having been annealed at 400° C.

In FIGS. 11-14 the performance of a sensing layer formed from lanthanum oxide (Code S3) is compared to the performance of a sensing layer formed from niobium pentoxide $Nb_2O_5$ (Code S1) and a sensing layer formed from neodymium oxide $Nd_2O_3$ (Code S2). As shown in FIGS. 12-14 and as summarized in FIG. 11 the sensing layer formed from lanthanum oxide has a higher average sensitivity for each of the three annealing temperatures of 25° C., 200° C., and 400° C.

The sensing effect of the sensing layer 136, in one embodiment, occurs in response to $OH^-$ hydroxyl groups of moisture combining with $La^{3+}$ cations on the surface of the lanthanum oxide resulting in a subsequent dissociation of the water molecule. The increase anion density leads to an increase in the density of holes in the semiconductor material, thereby decreasing the electrical resistance of the lanthanum oxide. The sensor device 102 uses this effect to produce a humidity sensor that exhibits a simple and fast change in electrical resistance as opposed to traditional humidity sensors, which are slow and complex.

Figure 15:
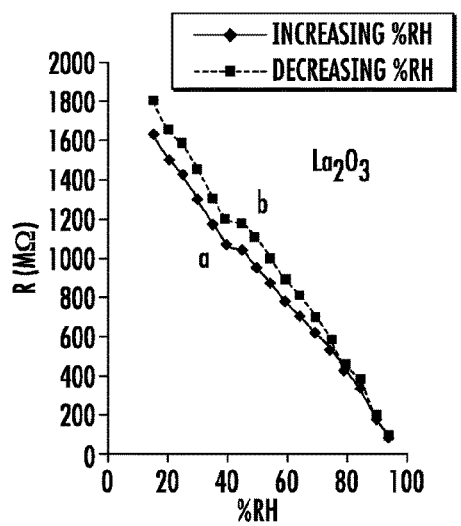
FIG. 15 is a graph of resistance versus percent relative humidity showing a hysteresis effect of a sensing layer formed from lanthanum oxide.
Figure 16:
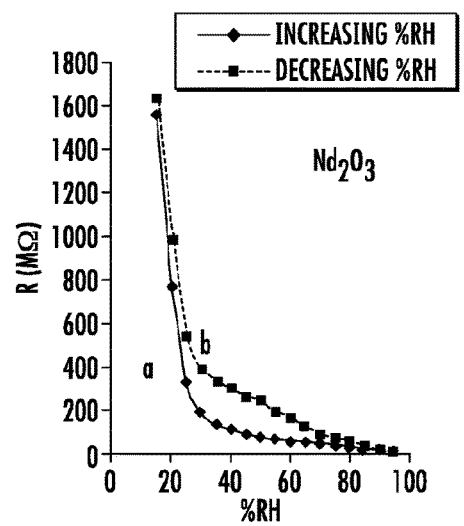
FIG. 16 is a graph of resistance versus percent relative humidity showing a hysteresis effect of a sensing layer formed from neodymium oxide.
Figure 17:
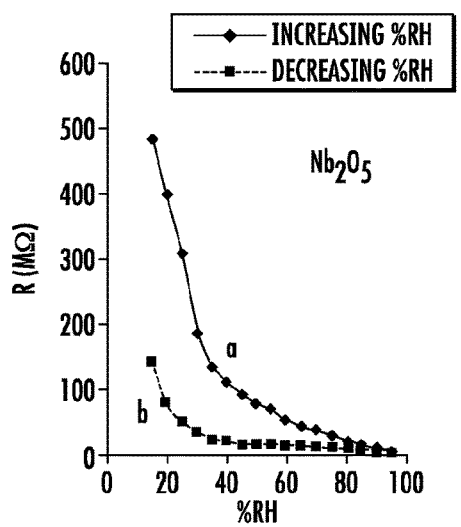
FIG. 17 is a graph of resistance versus percent relative humidity showing a hysteresis effect of a sensing layer formed from niobium pentoxide.

In FIGS. 15-17, the linearity and hysteresis exhibited by sensing layers formed from lanthanum oxide, niobium pentoxide, and neodymium oxide are shown in response to an increase in relative humidity from zero to one hundred percent and then a decrease in relative humidity from one hundred percent to zero. As shown by the graph of FIG. 16, the sensor layer formed from lanthanum oxide has the most linear response curve and exhibits the least amount of hysteresis. The reason that the lanthanum oxide layer exhibits hysteresis is due to the chemisorbed first layer of dissociated water molecules which, in some situations, may not be completely removed from the sensor layer as the relative humidity is decreased. To completely eliminate the hysteresis, heating of the sensing layer 136 with the heating layer 120 is effective to remove all/most of the chemisorbed first layer of dissociated water molecules. The tests that resulted in the graphs of FIGS. 16-18 were repeated three months later with the same lanthanum oxide sensor layer and substantially the same results were achieved, thereby confirming the robustness of the lanthanum oxide sensing layer 136. Accordingly, the sensor device 102 having the lanthanum oxide sensing layer 136 exhibits substantially no ageing effect and is a durable and long lived sensor device.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A thin film gas sensor device comprising:
   a substrate;
   a heater layer above the substrate;
   a non-suitable seed layer above the heater layer and supported by the substrate,
   a nanostructured thin film layer formed directly on the non-suitable seed layer using atomic layer deposition (ALD) and formed with a semi-conductor material including holes, wherein the semiconductor material is configured to undergo an increase in a density of the holes in the presence of a target gas thereby decreasing an electrical resistance of the nanostructured thin film layer; and
   a first and a second electrode supported by the substrate and operably connected to the nanostructured thin film layer such that the decrease in electrical resistance can be detected.

2. The thin film gas sensor device of claim 1, wherein:
   the nanostructured thin film layer is configured to undergo the decrease in the electrical resistance during a time constant, and
   the time constant is less than one second.

3. The thin film gas sensor device of claim 1, wherein the nanostructured thin film layer is non-organic and does not include polyimide or other polymers.

4. The thin film gas sensor device of claim 1, wherein the nanostructured thin film layer is formed from lanthanum oxide and the target gas is water vapor.

5. The thin film gas sensor device of claim 1, wherein:
   the nanostructured thin film layer defines a plurality of grain boundaries formed by spaced-apart nucleation on the non-suitable seed layer, and
   air spaces are defined between at least some grains of the plurality of grains.

6. A method of fabricating a thin film gas sensor device comprising:
   providing a substrate;
   forming a heater layer above the substrate;
   forming a non-suitable seed layer above the heater layer;
   supporting a first electrode with the substrate;
   supporting a second electrode with the substrate;
   forming a nanostructured thin film layer using atomic layer deposition (ALD) directly on the non-suitable seed layer using a semi-conductor material including holes, wherein the semiconductor material is configured to undergo an increase in a density of the holes in the presence of a target gas thereby decreasing an electrical resistance of the nanostructured thin film layer; and
   operably connecting a first and a second electrode to the nanostructured thin film layer such that the decrease in electrical resistance can be detected.

7. The method of claim 6, further comprising:
   forming the nanostructured thin film layer from lanthanum oxide, such that the decrease in electrical resistance occurs in response to the target gas including water vapor.

8. The method of claim 6, further comprising:
   forming the nanostructured thin film layer so as to cause the nanostructured thin film layer to undergo the decrease in electrical resistance during a time constant of less than one second.

9. The method of claim 6, further comprising:
   forming the nanostructured thin film layer with non-organic material and without polyimide or other polymers.

10. The method of claim 6, further comprising:
    forming the first electrode and the second electrode directly on the non-suitable seed layer.

11. The method of claim 6, wherein forming the nanostructured thin film layer further comprises:
    forming a plurality of grains of the nanostructured thin film layer by spaced-apart nucleation of the semiconductor material of the nanostructured thin film layer on the non-suitable seed layer.

12. The method of claim 11, further comprising:
    structuring the non-suitable seed layer to encourage the spaced-apart nucleation of the plurality of grains of the sensing layer.

13. The method of claim 12, wherein structuring the non-suitable seed layer comprises:
    ion-milling or chemically activating the non-suitable seed layer.

* * * * *